(12) United States Patent
Gibson et al.

(10) Patent No.: US 8,813,747 B2
(45) Date of Patent: Aug. 26, 2014

(54) VAPORIZER SYSTEM FOR DELIVERY OF INHALABLE SUBSTANCES

(75) Inventors: Nathaniel Gibson, Pawlet, VT (US); Michael Hexter, Tarzana, CA (US); Kent Sands, New York, NY (US)

(73) Assignee: HexBG, LLC, Pawlet, VT (US)

( * ) Notice: Subject to any disclaimer, the term of this patent is extended or adjusted under 35 U.S.C. 154(b) by 594 days.

(21) Appl. No.: 12/851,873

(22) Filed: Aug. 6, 2010

(65) Prior Publication Data

US 2011/0030706 A1    Feb. 10, 2011

Related U.S. Application Data

(60) Provisional application No. 61/273,738, filed on Aug. 7, 2009.

(51) Int. Cl.

| | |
|---|---|
| A62B 9/02 | (2006.01) |
| A62B 9/04 | (2006.01) |
| A24F 1/02 | (2006.01) |
| A24F 5/04 | (2006.01) |
| A24F 13/04 | (2006.01) |
| F16K 1/00 | (2006.01) |
| F16K 15/00 | (2006.01) |
| F23D 11/00 | (2006.01) |
| F23D 14/00 | (2006.01) |
| A61M 11/04 | (2006.01) |
| F22B 1/28 | (2006.01) |

(52) U.S. Cl.
CPC ........... *A61M 11/041* (2013.01); *A61M 11/042* (2014.02); *F22B 1/28* (2013.01); *A61M 2205/07* (2013.01)
USPC ............ 128/205.24; 128/202.27; 128/203.26; 251/322; 131/223

(58) Field of Classification Search
CPC ............ A61M 11/041; A61M 11/042; A61M 2205/07; F22B 1/28
USPC .......................... 128/202.27, 203.12, 203.17, 128/203.26–28, 204.17, 205.24; 251/319–322; 131/191, 194, 206, 223, 131/251.1, 273, 215.1
See application file for complete search history.

(56) References Cited

U.S. PATENT DOCUMENTS

| | | | |
|---|---|---|---|
| 2,086,140 | A | 7/1937 | Silten |
| 3,115,134 | A | 12/1963 | Schmahl |

(Continued)

FOREIGN PATENT DOCUMENTS

| | | |
|---|---|---|
| EP | 1867375 | 12/2007 |
| WO | 0005976 | 2/2000 |

OTHER PUBLICATIONS www.dabuddhavaporizer.com/ceramic-heater.html (Jan. 13, 2009).

*Primary Examiner* — Tan-Uyen T Ho
*Assistant Examiner* — Mark K Han
(74) *Attorney, Agent, or Firm* — Downs Rachlin Martin PLLC

(57) ABSTRACT

A vaporizer system that supplies clean, heated air to vaporizable material by directing ambient air from an area surrounding the vaporizer system through a secure air passageway that leads the air through a pump, a heat source, and then onto the vaporizable material. The air passageway prevents the interaction of the air with possibly emissive components. The heated air drives out active ingredients from the vaporizable material, which may be subsequently captured in a removable container or inhaled directly. The vaporizer system includes an air chamber surrounding the receptacle for receiving the material to be vaporized which isolates the material from environmental disturbances. The removable container attaches to a valve, which attaches to the top of the vaporizer system. The valve is configured to be operable between three positions with the use of only one finger and a thumb of one hand.

34 Claims, 8 Drawing Sheets

(56) References Cited

U.S. PATENT DOCUMENTS

| | | | | |
|---|---|---|---|---|
| 3,820,540 A | | 6/1974 | Hirtz et al. | |
| 4,083,374 A | * | 4/1978 | Jacobsen | 131/178 |
| 4,161,954 A | * | 7/1979 | Fornaciari | 131/173 |
| 4,198,992 A | * | 4/1980 | Smith | 131/330 |
| 4,214,146 A | | 7/1980 | Schimanksi | |
| 4,278,099 A | * | 7/1981 | Jacobsen | 131/178 |
| 4,579,141 A | | 4/1986 | Arff | |
| 4,604,999 A | | 8/1986 | Maeda | |
| 4,756,347 A | | 7/1988 | Hagan et al. | |
| 4,948,092 A | | 8/1990 | Kasper et al. | |
| 6,095,153 A | | 8/2000 | Kessler et al. | |
| 6,250,301 B1 | | 6/2001 | Pate | |
| 6,513,524 B1 | | 2/2003 | Storz | |
| 6,742,681 B1 | | 6/2004 | Yang | |
| 6,877,640 B1 | * | 4/2005 | Frushone | 222/158 |
| 7,195,029 B2 | | 3/2007 | Wass | |
| 7,475,684 B2 | | 1/2009 | Balch et al. | |
| 7,552,730 B2 | | 6/2009 | Kates | |
| 7,624,734 B2 | | 12/2009 | Balch et al. | |
| 2004/0065324 A1 | | 4/2004 | Pivinski | |
| 2005/0279353 A1 | | 12/2005 | McCoy | |
| 2007/0240715 A1 | | 10/2007 | Hill | |
| 2008/0029099 A1 | | 2/2008 | Storz | |
| 2009/0078253 A1 | | 3/2009 | Bao | |

* cited by examiner

VAPORIZER SYSTEM FOR DELIVERY OF INHALABLE SUBSTANCES

RELATED APPLICATION DATA

This application claims the benefit of priority of U.S. Provisional Patent Application Ser. No. 61/273,738, filed Aug. 7, 2009, and titled AROMATHERAPY VAPORIZER SYSTEM FOR EXTRACTING ACTIVE ELEMENTS FROM BIOMASS which is incorporated by reference herein in its entirety.

FIELD OF THE INVENTION

The present invention generally relates to the field of hot air vaporizers.

BACKGROUND

Herbal substances are known to be used as remedies for various ailments or for pleasure. Most often, herbal substances are ingested in the form of pills, tablets, brewed as teas, or by eating the plant itself. However, these methods are generally inefficient and/or ineffective as the herbs necessarily undergo biological degradation, via, for example, a person's stomach, before entering the bloodstream.

Inhaling an herbal substance is a fast and effective way to introduce the active ingredients in the substance into the bloodstream. Two methods are typically used for inhaling herbal substances: smoking and vaporizing. In general, smoking involves the pyrolysis of herbs or other materials. The most common example of smoking an herbal substance is the use of a cigarette to ingest tobacco. As the tobacco is burned and inhaled, its active ingredients are transported into the body's bloodstream through the lungs. In addition to the active ingredients, however, the pyrolysis of tobacco also releases harmful byproducts such as tar, carbon monoxide, ash, and other carcinogenic derivatives. These byproducts and the heat associated with combustion account for many of the ill-health effects of smoking.

In contrast, the process of vaporizing an herbal substance can provide a healthier alternative for active ingredient delivery. Vaporizers generally cause the atomization of water, medicine, or other substances into a heated air flow. When used to release the active ingredients of tobacco or other herbal materials, a vaporizer directs hot air through the plant material at a temperature sufficient to release the active ingredients into the air flow, but not so high as to combust the material. Preventing combustion reduces the incidence of the irritating and harmful effects of smoking because the vaporization process produces only negligible amounts of tar, carbon monoxide, or other harmful constituents.

Certain known vaporizers draw into the hot air used to vaporize the herbal substance potentially harmful gases emitted by components of the vaporizer such as the heater. Ingestion of such harmful gases into the lungs is inconsistent with the therapeutic benefits the vaporizer is intended to provide. Another drawback with some prior art vaporizers is that it tends to be difficult to install and remove the container used to receive the vapor. Yet other vaporizers are designed in a way that makes it difficult to conveniently remove vapor from the container in which it is captured. In some cases two-handed operation is required, and in other cases a separate mouthpiece must be installed after the container housing the vapor is removed from the vaporizer.

SUMMARY OF THE DISCLOSURE

In a first aspect, an embodiment of the present invention is directed to a vaporizer system comprising: a housing, a heater disposed within the housing, a stem coupled to the housing, a receptacle for receiving material to be vaporized, the receptacle interposed between the heater and the stem; and a valve releaseably coupled to the stem.

In a second aspect, an embodiment of the present invention is directed to a valve for use with a vaporizer having a structure for exhausting vapor, the valve comprising: a body having an opening for receiving the structure of the vaporizer, a clamping assembly associated with the body so as to be in communication with the opening, wherein the clamping assembly is movable between a first position, in which the clamping assembly cooperates with the structure to releasably secure the body thereto when the structure is present in the opening, and a second position, in which the body may be moved freely on and off the structure, a mouthpiece in fluid communication with the opening so that vapor may be drawn through the opening via the mouthpiece, and a connector for securing a vapor-receiving container to the body proximate the opening.

In a third aspect, an embodiment of the present invention is directed to a vaporizer system comprising: a housing having an interior, a receptacle for receiving a material to be vaporized, a heater disposed in the interior of the housing, an air passageway occupying a first portion of the interior of the housing and extending from a region adjacent the housing to the receptacle, the air passageway for conveying air from the region to the receptacle in fluid isolation with respect to portions of the interior other than the first portion, the air passageway including a first section surrounding the heater and in thermal communication therewith so that heat generated by the heater may be transferred to air in the first section, and a pump in fluid communication with the air passageway for causing air in the air passageway to move toward the receptacle, wherein the pump is disposed in the housing.

In a fourth aspect, an embodiment of the present invention is directed to a method of consuming active ingredients of a vaporizable material, the method comprising: inserting a quantity of the vaporizable material into a vaporizer, propelling heated air through the vaporizable material to release and entrain at least some of the active ingredients of the vaporizable material in a vapor stream, directing the vapor stream through a valve and into a container coupled to the valve, removing the valve and container from the vaporizer, and opening the valve with one hand of a user and removing vapor out the container through the valve while the valve remains coupled to the container.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
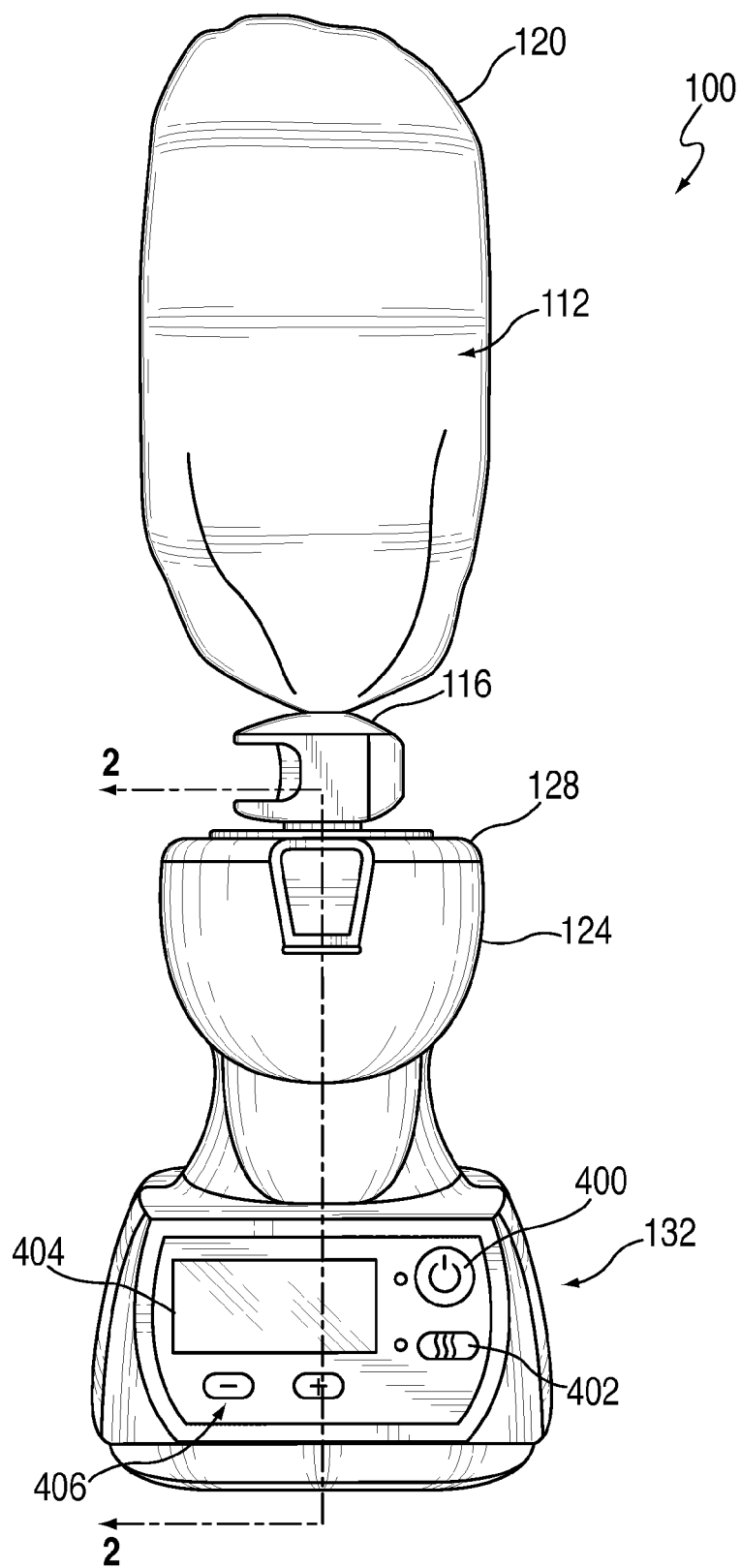
FIG. 1 is a perspective view of a vaporizer system according to an embodiment of the present invention.
Figure 2:
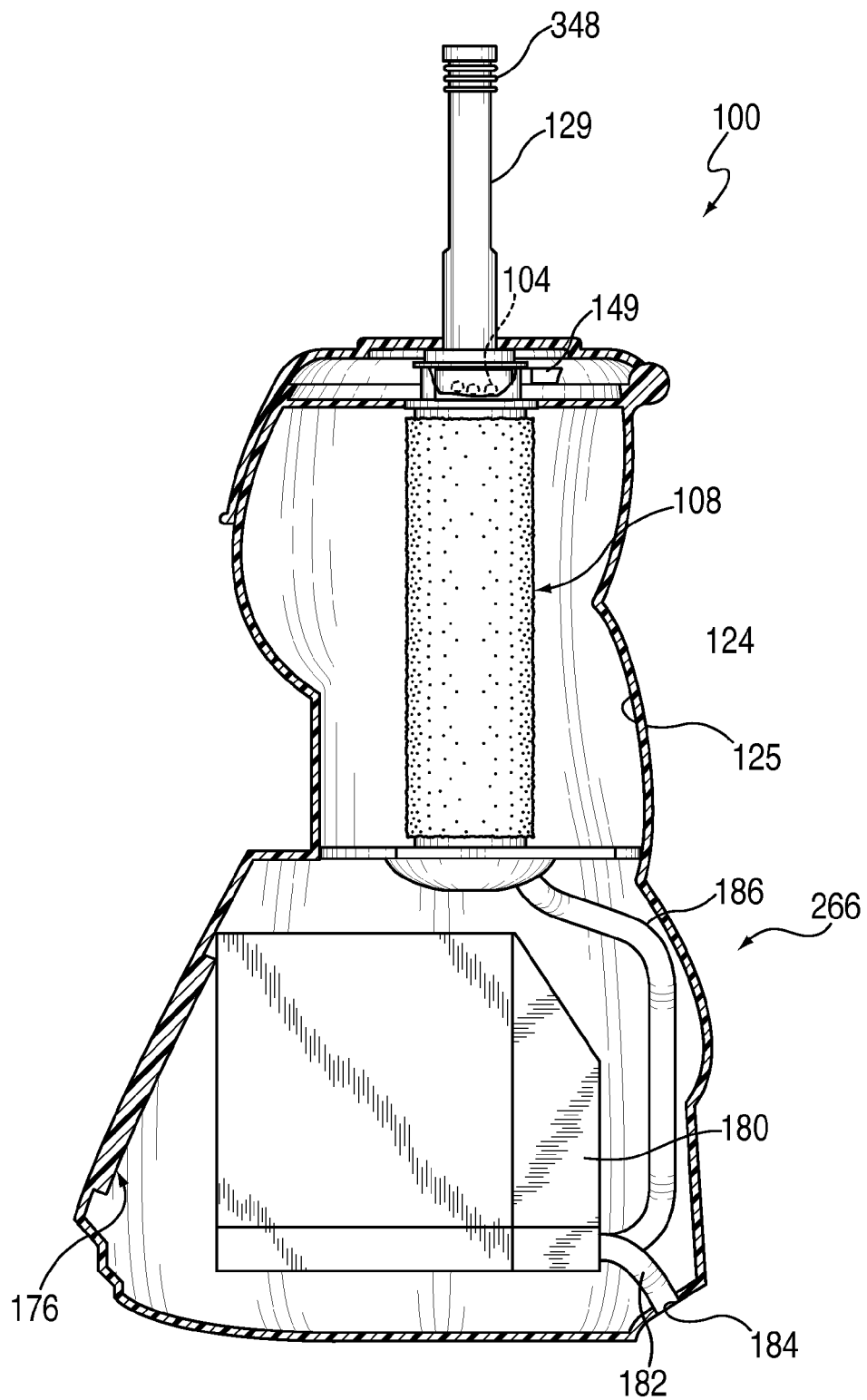
FIG. 2 is a partial cross-sectional view of the vaporizer system shown in FIG. 1, taken along line 2-2 in FIG. 1, showing some internal components of the vaporizer system in non-cross-sectional form.

Referring now to the drawings, FIGS. 1 and 2 illustrate an exemplary vaporizer system 100 in accordance with certain aspects of the present invention. Generally, vaporizer system 100 is a device suitable for generating and propelling hot air through a vaporizable material 104, e.g., tobacco. As will be discussed more fully below, vaporizer system 100 produces a resultant vapor 112 from vaporizable material 104 using external air that is delivered to the vaporizable material so as to avoid the inclusion of any harmful gases or particulate matter, if any, that might be released from heat source 108 or other components of the vaporizer system. Vaporizer system 100 also shields vaporizable material 104 with a chamber of hot air, thus reducing temperature fluctuations and allowing for more uniform heating of the vaporizable material during the vaporization process. In addition, vaporizer system 100 permits the single-handed operation of a valve 116 that is coupled to a container 120 holding vapor 112, thus enhancing ease and flexibility of use of the vaporizer system.

Figure 3:
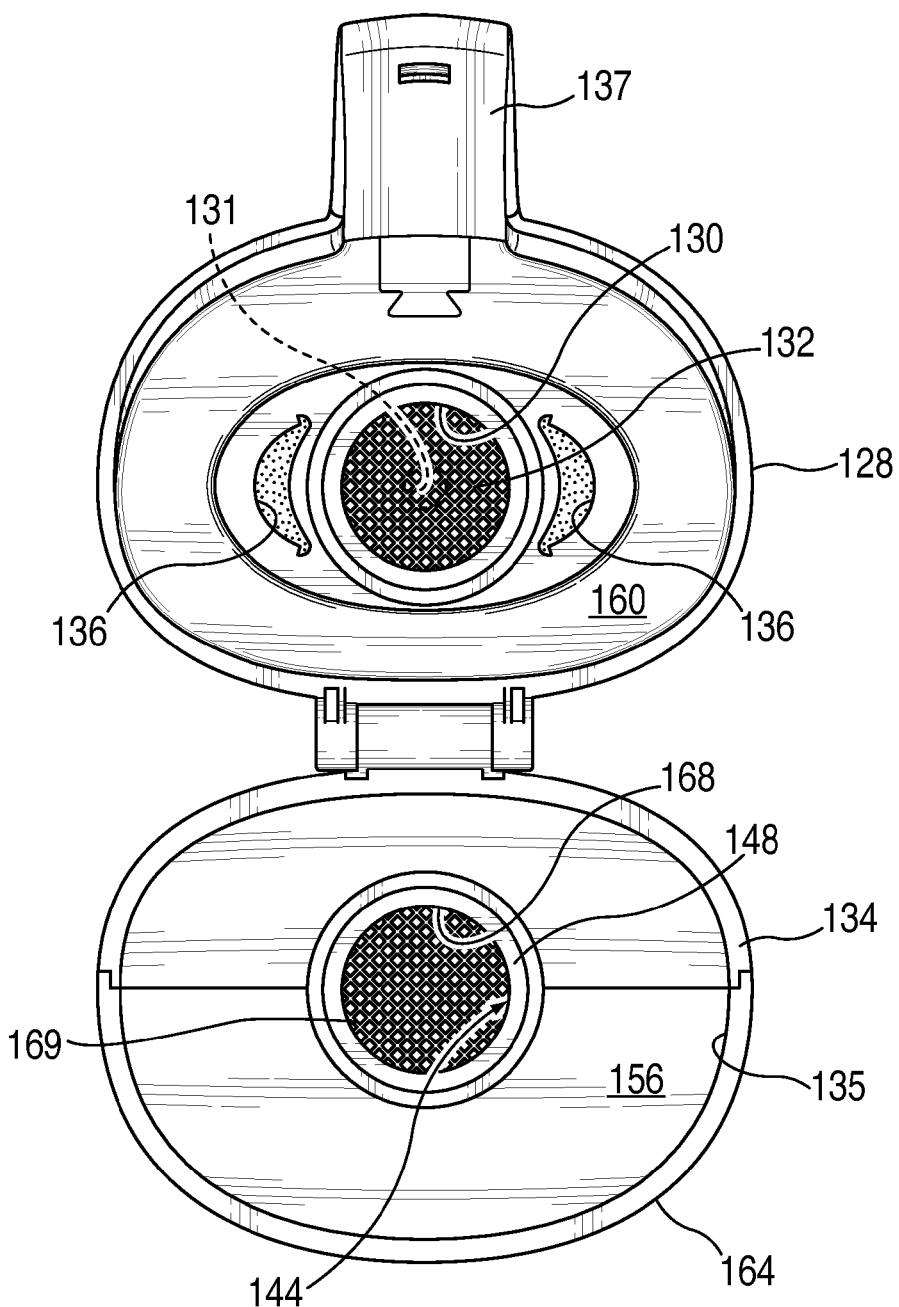
FIG. 3 is a top view of the vaporizer system shown in FIG. 1, with the lid shown in the open position to reveal an upper interior chamber of the vaporizer system.

Referring now to FIGS. 1-3, vaporizer system 100 includes a housing 124 having a hollow interior cavity 125 in which various components of the vaporizer system are positioned. Vaporizer system 100 may also include a lid 128 that is pivotally mounted to an upper portion of housing 124 so as to be moveable between a closed position, as shown in FIG. 1, and an open position, as shown in FIG. 3. Lid 128 may include an upstanding stem 129 on which valve 116 and container 120 may be releasably mounted. Lid 128 may include a bore 130 (FIG. 3) that is in fluid communication with a bore 131 (FIG. 3) in stem 129. Optionally, a screen 132 may be positioned in bore 130 to block the passage of vaporizable material 104 up and through bore 131 in stem 129. Lid 128 is sized and configured so as to engage an upper edge 134 (FIG. 3) of housing 124 when in the closed position, thereby substantially isolating upper interior chamber 135 in housing 124 from the region surrounding the housing. If desired, vents 136 (FIG. 3) may be provided in lid 128 to allow some ventilation of interior chamber 135. Lid 128 may also include a clasp 137 or other fastener to releasably secure the lid in the closed position.

Housing 124 includes various controls 132 (described further below) used in the operation of vaporizer system 100.

Vaporizer system 100 includes a receptacle 144 for receiving vaporizable material 104. As discussed more below, in one embodiment receptacle 144 may be defined by a cavity provided in top portion 148 of heat source 108. In another embodiment, receptacle 144 may include a removable basket 149 (FIG. 2) for solid materials or crucible (not shown) for liquid material that is sized to be received in top portion 148 of heat source 108 or elsewhere in or on housing 124. If desired, an opening (not shown) may be provided in housing 124 adjacent top portion 148 to allow vaporizable material 104, typically positioned in a basket 149 or other container (e.g., a drawer), to be slid in or removed from a region above aperture 168.

Interior chamber 135 provides an insulating air region around receptacle 144 that shields the receptacle from cold, breezes and other environmental effects that might change the temperature of vaporizable material 104 in the receptacle. In an exemplary embodiment, upper interior chamber 135 is defined substantially by a bottom portion 156, a top portion 160, and a sidewall portion 164 extending between bottom portion and top portion. In this embodiment, top portion 160 is defined by the inner surface of lid 128. Bottom portion 156 includes an aperture 168 extending therethrough. If desired, a screen 169 may be positioned in aperture 168 to block vaporizable material 104 from dropping through aperture 168 while simultaneously allowing heated air to be delivered upwardly through the aperture, as discussed more below. Typically, receptacle 144 is located in top portion 148 just above aperture 168. Aperture 168 provides an opening for hot air coming from heat source 108 to intercept receptacle 144, as discussed more below. Other locations for receptacle 144 within the path of heated air provided by heat source 108 are also encompassed by the present disclosure.

Vaporizer system 100 includes a pump 180 (FIG. 2) for providing an air flow to heat source 108 in an amount that (i) corresponds to the heating capability of the heater source and (ii) will fill container 120 in a reasonable amount of time. In an exemplary embodiment, pump 180 is capable of providing an air flow of about 0.80 cubic feet per minute (cfm), which when used in vaporizer system 100, corresponds to a heat transfer rate of about 15 watts/cfm to about 19 watts/cfm. Pump 180 draws air from the region surrounding housing 124 via a tube 182 or other air passageway connected to an opening 184 in housing 124. Pump 180 delivers pressurized air to heat source 108 via a tube 186 or other air passageway.

Figure 4:
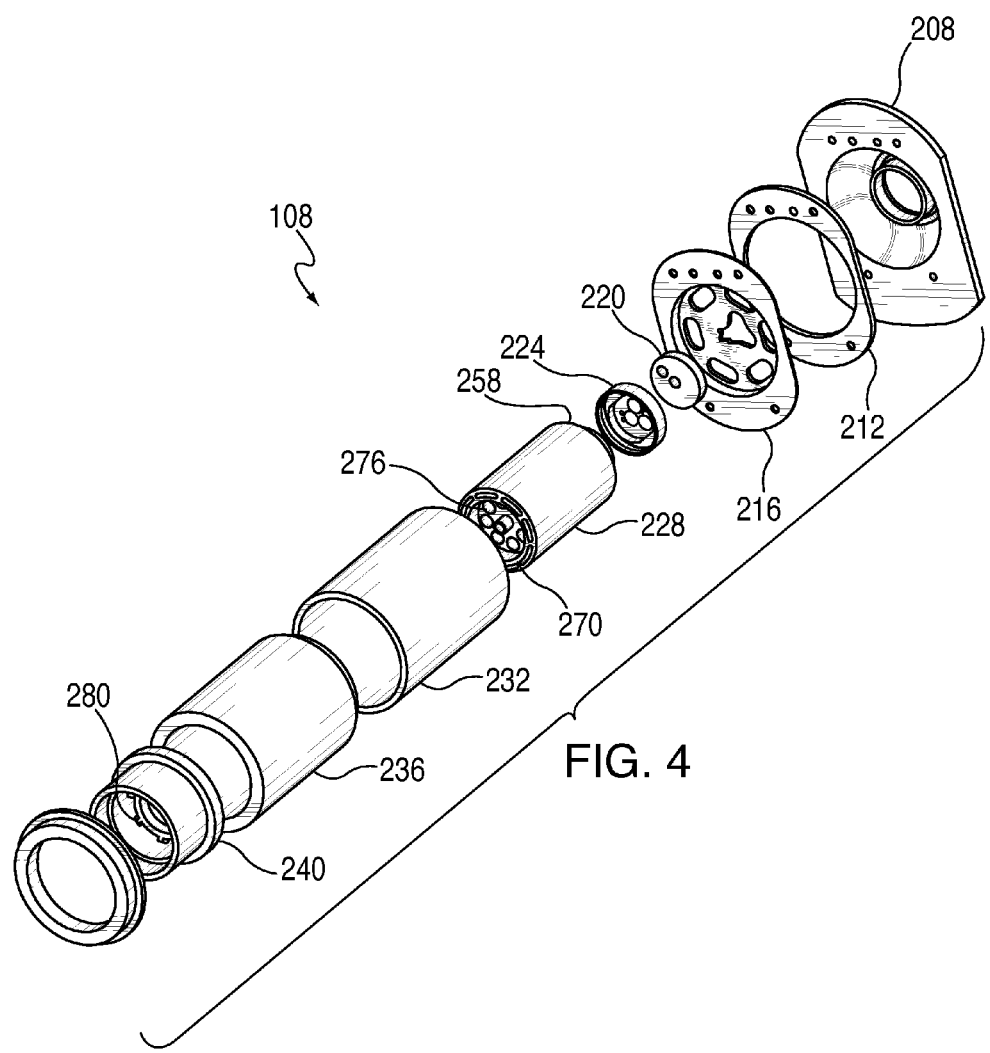
FIG. 4 is an exploded perspective view of a heat source according to an embodiment of the present invention.

FIG. 4 shows in exploded perspective view an exemplary heat source 108 suitable for use in a vaporizer system, such as vaporizer system 100. Generally, heat source 108 provides for the efficient and uniform heating of air provided, for example, by pump 180, while substantially eliminating any entrainment of undesired vapors or other emissions from the heating element (described further below in reference to FIG. 6) in heat source 108 or from other potentially emissive components 176 (FIG. 2) in cavity 125 of housing 124 in the incoming air delivered to receptacle 144. In one embodiment, heat source 108 includes an air intake 208, a lower gasket 212, a foundation element 216, a lower wire guide 220, an upper wire guide 224, a heater 228 with at least one heating element 230 (FIG. 6), a first insulator 232, a second insulator 236, and flow director 240. Heating element 230 may, for example, include a resistive heating element.

Figure 5:
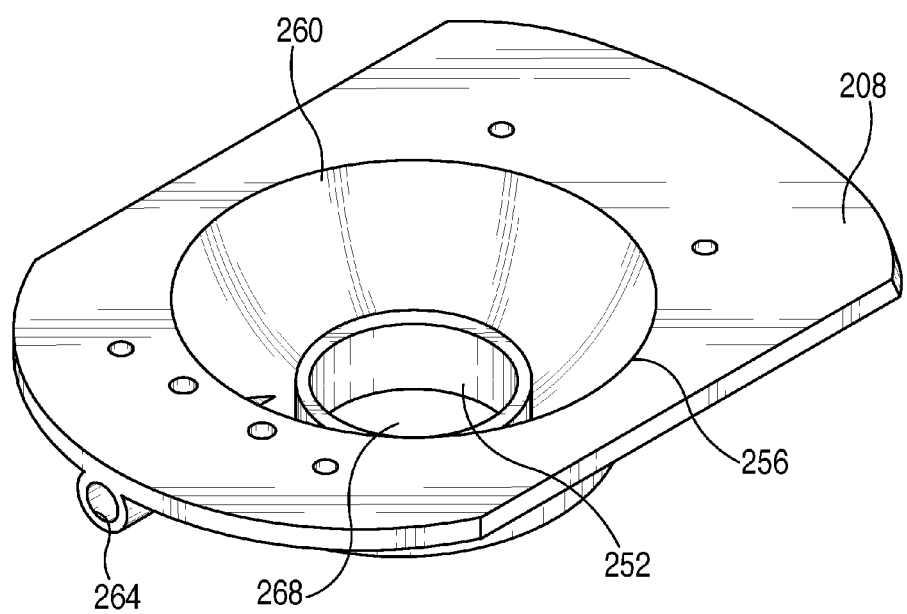
FIG. 5 is a perspective view of an air intake according to an embodiment of the present invention.

As shown in FIGS. 4 and 5, air intake 208 aids in substantially eliminating the interaction between potentially harmful vapors emitted by (i) heating element 230 (FIG. 6) and by other potentially emissive components 176 (e.g., semiconductor chips and other devices attached to printed circuit boards located in housing 124) and (ii) the incoming ambient air that is heated by heater 228 as such air passes through one or more air ducts 248 (best seen in FIG. 6) in the heater. With particular reference to FIG. 5, in an exemplary embodiment, air intake 208 has a generally hemi-torus shape with an inner edge 252 and an outer edge 256 that together form the boundary for a depression 260. Inner edge 252 and outer edge 256 are sized and configured to engage an end 258 of heater 228 so that air ducts 248 are in fluid communication with air present in depression 260, and other portions of the heater, including heating element(s) 230, are fluidly isolated from the air in depression 260.

Figure 6:
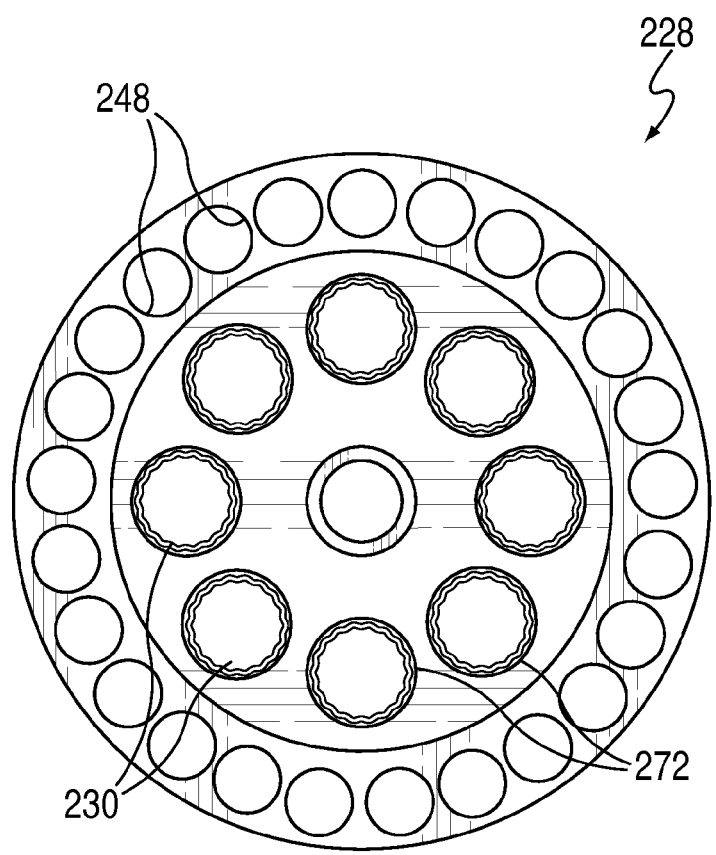
FIG. 6 is a cross-sectional view of a heat source according to an embodiment of the present invention.

Although FIGS. 4 and 5 show air intake 208 as having a hemi-torus configuration, air intake 208 may be configured into other hemi-toroid shapes or other forms known in the art that allow for the separation between the ambient air external to heat source 108 that is traveling to air ducts 248 and air surrounding heating element 230 (FIG. 6). Generally, the configuration of air intake 208 is dependent upon the configuration of heater 228. For example, if heater 228 is generally cylindrical in shape with air ducts 248 being located closer to the central axis of the heater than heating element 230, air intake 208 may be shaped as a hemi-sphere that is configured to correspond with the area encompassed by the air ducts.

Air intake 208 includes an air inlet 264 that extends through a portion of the wall forming depression 260. Air inlet 264 may be connected to tube 186 and provides a pathway for the ambient air present outside housing 124 (FIGS. 1 and 2) to enter depression 260, via tube 182, pump 180, and tube 186 on its way to air ducts 248 (FIG. 6). With this combination of elements, an air passageway 266 is created between the region surrounding vaporizer system 100 and receptacle 144. In one embodiment, passageway 266 includes opening 184, tube 182, pump 180, tube 186, and air ducts 248 in heater 228.

In the exemplary embodiment described above, air intake 208 also includes an aperture 268 through which the wires for heating element 230 enter heater 228. In certain embodiments, heater 228 may additionally include one or more heating element wire guides, such as a lower wire guide 220 and upper wire guide 224, for securing the heating element within heat source 108. Additionally, and as shown in FIG. 4, lower gasket 212 and foundation element 216 aid in securing air intake 208 to heater 228 and in sealing the air intake to the heater. While the aforementioned components aid in reducing interaction between ambient air to be used in the vaporization process and the undesirable fumes that may be released by heating element 230 and other emissive components 176 located inside housing 124, other devices known in the art or combinations of the components described above may provide the secure seal between air intake 208 and heater 228.

As shown in FIG. 6, in one embodiment heater 228 may have a generally cylindrical configuration and may be made from one or more blocks of material having desired properties. These properties include relatively good electrical insulation, a relatively high thermal conductivity and sufficiently high mechanical strength to support heating element 230 and generally withstand typical shock, vibration and other forces to which vaporizer system 100 will typically be subjected, e.g., an alumina ceramic. In this embodiment, air ducts 248 and heating chambers 272 are formed to extend through the entire axial length of the cylindrical block(s) or other structure used in the core of heater 228, and can be equidistantly spaced in a circular configuration inside the outer periphery of the heater to provide for uniform heating of the incoming air. In an exemplary embodiment, a plurality of air ducts 248 surround a plurality of heating chambers 272, so as to provide uniform heating of the air. The size, configuration and relative spacing of air ducts 248 and heating chambers 272 may be determined via several factors readily understood in the art such as, but not limited to, the expected air flow through the air ducts during operation of heat source 108, the size of heater 228, the heat output capacity of heating element 230, and the type of material used in the cylindrical block(s) or other structures used in the heater. In any event, the size and configuration of air ducts 248 and heating chambers 272 should be selected to provide efficient and uniform heating of the ambient air entering the heater through air intake 208.

In an exemplary embodiment, and as shown in FIG. 6, heating element 230 is disposed radially inwardly of air ducts 248. This configuration allows for more efficient transfer of heat to the air traversing plurality of air ducts 248 because the heat generated by heating element 230 radiates radially outward through heater 228 and intersects the plurality of air ducts before reaching the outer boundary of the heater. To retain the heat generated by heating element 230 in heater 228, insulating members, e.g., first insulator 232 and second insulator 236 (FIG. 4), may be provided to limit the escape of heat to interior cavity 125 of housing 124.

Heating element 230 is typically composed of materials capable of achieving high temperatures when connected to an electrical current, such as a high-resistance metal alloy. In an embodiment of heating source 108, heating element 230 is a continuous wire that is threaded through the heating chambers 272, e.g., up through one heating chamber 272, down through the next heating chamber, up through the next heating chamber, and so on. In this embodiment, and as shown in FIG. 4, heater 228 may be constructed as two concentric cylinders that are axially offset such that a lip 270 is formed that extends around the upper edge of the heater forming a recess 276. Recess 276 aids in the separation of the heating element 230 from the air exiting heater 228 by allowing for the heating element wires to be sealed away from the exiting air. In an alternative embodiment, a plurality of heating elements 230 may be used, such that an individual heating element is placed into each heating chamber 272.

With reference to FIGS. 2-4, in one embodiment flow director 240 defines top portion 148 of heater 228, i.e., the end of the heater opposite air intake 208. Flow director 240 assists in directing the air exiting heater 228 to the material to be vaporized. As shown in FIG. 4, flow director 240 has a generally cylindrical configuration with a hollow interior sized and configured to define receptacle 144 in which vaporizable material 104 is received. Flow director 240 also ensures that receptacle 144 is substantially centered above heater 228, thus providing for more uniform heating of vaporizable material 104. In an embodiment, flow director 240 may also include a seal 280 (FIG. 4) partially enclosing the end of the flow director proximate heater 228. Seal 280 prevents the interaction of air that has come into contact with heating element 230 with the air exiting heater 228.

Figure 7A:
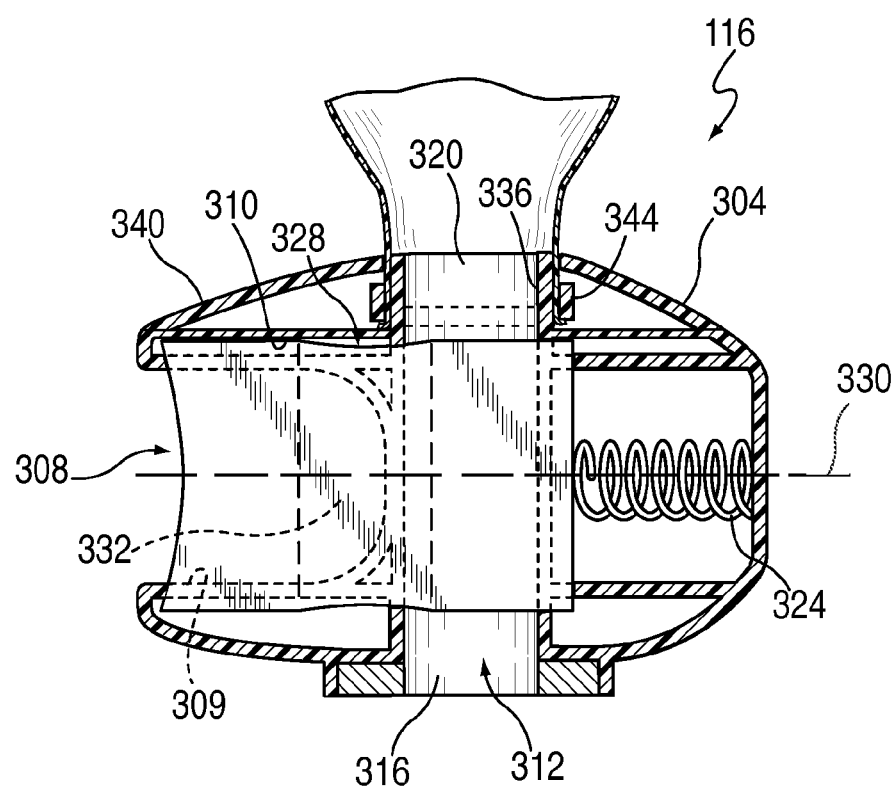
FIG. 7A is a cross-sectional view of a valve in an closed position according to an embodiment of the present invention.
Figure 7B:
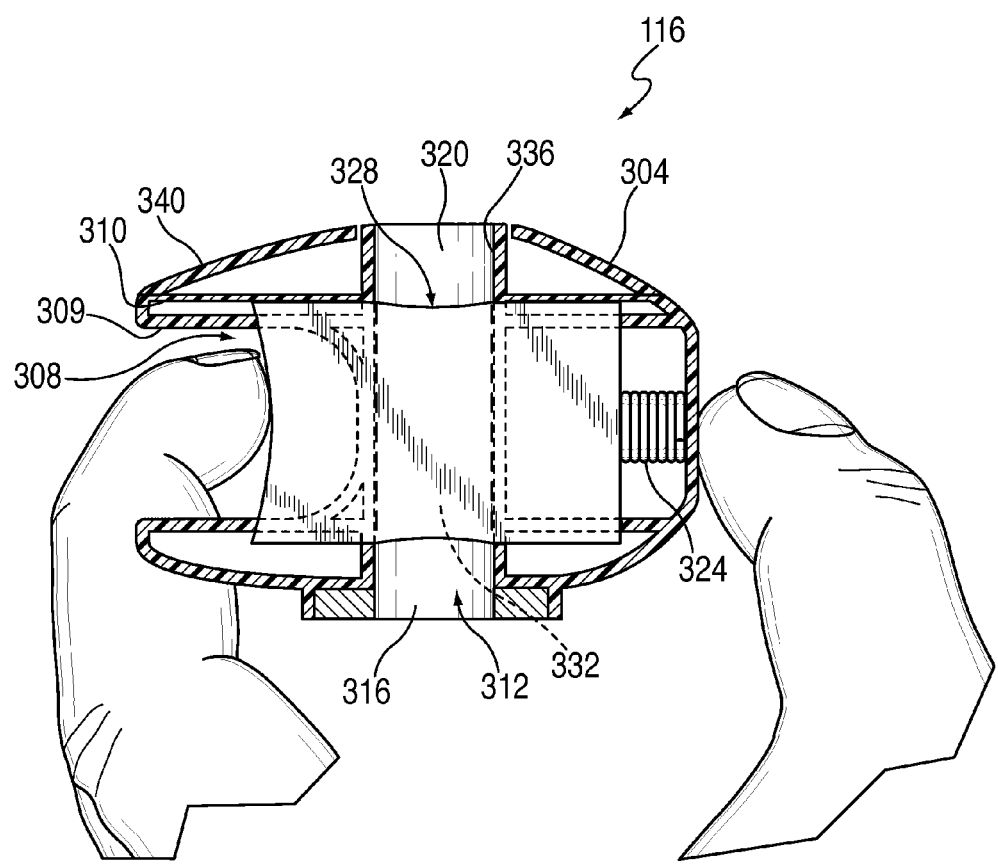
FIG. 7B is a cross-sectional view of the valve shown in FIG. 7A in the open position.

Turning now FIGS. 7A and 7B, as discussed above, vaporizer system 100 includes a valve 116. The latter may be a dual-purpose valve assembly for the introduction and removal of herbal vapor from a container coupled to the valve, such as container 120. In an exemplary embodiment, valve 116 includes a valve body 304 that contains a clamping assembly 308.

Valve body 304 is sized and configured to allow for one-handed operation of valve 116. In an exemplary embodiment, valve body 304 has a generally ellipsoid shape, with access to clamping assembly 308 being provided via opposing slots 309 (only one of which is illustrated) proximate an end of the valve body. Opposing slots 309 communicate with an interior cavity 310 in which clamping assembly 308 resides. This configuration allows a user to depress a portion of clamping assembly 308 with a thumb or forefinger, which is received in slots 309 and interior cavity 310, while the remainder of valve 116 may be stabilized by the user's palm and remaining fingers.

Valve body 304 also has an opening 312 extending therethrough. One end of opening 312 defines an inlet 316 (coming from housing 124 (FIG. 1)) and the other end defines an outlet 320 (going to container 120 (FIG. 1)). Valve body 304 may also, in certain embodiments, include a valve lid 340, which may house a connector 344 for coupling container 120 (FIG. 1) to valve 116 at a generally annular wall 336 that makes up a top portion of outlet 320. The means and the method of connecting valve body 304 and container 120 are known in the art and include elastic bands, zip-ties, and other devices that are suitable for creating a secure, relatively air-tight connection. In an exemplary embodiment, where container 120 is a heat-resistant plastic bag having an opening sized to cooperate with opening 312, connector 344 may be a zip tie that resides under valve lid 340.

Clamping assembly 308 includes a biasing member 324 and a plug 328. Biasing member 324 may be a spring or other biasing device that applies a force in a direction parallel to axis 330 sufficient to drive plug clamping assembly 308 along this axis to a substantially closed position (as shown in FIG. 7B). In this regard, plug 328 is sized and configured to move back and forth in interior cavity 310 along axis 330 between the closed position illustrated in FIG. 7A and the open position illustrated in FIG. 7B. Plug 328 includes an opening 332 extending through the plug, e.g., a cylindrical bore. Opening 332 is sized and positioned so that when clamping assembly 308 is urged to the open position (as shown in FIG. 7B), thereby opening valve 116, opening 332 is aligned with opening 312, and so is additionally aligned with inlet 316 and outlet 320. Opening 312 and opening 332 are sized so that when plug 328 is in the open position, stem 129 on lid 120 may be received within these two openings. In this regard, openings 312 and 332 are typically sized so that stem 129 occupies substantially the entire volume contained within the openings.

Stem 129 may be tapered to have a smaller diameter at a point furthest from housing 124 than it does at the end proximate the housing. The taper of stem 129 can ease the insertion and removal of valve 116. Stem 129 may additionally include one or more gaskets 348, typically composed of silicone, having one or more ridges or flanges that aid in providing an airtight seal between the stem and the valve 116.

During a mode of operation of an exemplary vaporizer system 100 using valve 116, clamping assembly 308 may be urged to the open position illustrated in FIG. 7B by pressing plug 328 into interior cavity 310 against the bias of biasing member 324 until openings 312 and 332 are aligned. Next, valve 116 is placed on stem 129 on lid 128 so that the stem is fully received in openings 312 and 332. After the user releases plug 328, the latter is driven by biasing member 324 toward the closed position (FIG. 7A). Before reaching the closed position, however, stem 129 engages the sidewall of valve body defining opening 312 so as to provide a substantially airtight passage for vapors 112 traveling from housing 124 to container 120. This intermediate position of plug 328 is typically nearly the same as the open position, although in many embodiments the intermediate position will deviate slightly from the fully open position (in the direction of the closed position).

Valve 116 (FIGS. 7A-B) can also serve as a mouthpiece for the retrieval of vapors 112 from container 120 (FIG. 1) by the user. To function as a mouthpiece, the user depresses clamping assembly 308, thus aligning opening 332 with inlet 316 and outlet 320. The user then presses his or her lips to inlet 316 and breaths in, thus removing some of vapor 112 residing within container 120.

Discussing other aspects of the use of vaporizer system 100, the system is activated, typically by pressing or toggling an on/off switch 400 located in controls 132, which is typically positioned on the exterior of housing 124. The user also has the option of choosing a temperature setting for the vaporization process. Heat controls 406 allow for selection of the temperature output of heat source 108. Vaporizer system 100 may also include an indicator 404, which tells the user when heat source 108 has reached the desired temperature. While heat source 108 is warming, receptacle 144 may be filled at least partially with vaporizable material 104. Then, the user activates pump 180 with pump switch 402, which moves air from the region surrounding housing 124, through air intake 184 and into heater 228, and then subsequently through the vaporizable material 104 resting in receptacle 144. The heated air releases the active ingredients of vaporizable material 104 resulting in vapor 112, which flows into container 120 under the pressure provided by pump 180.

As described above with reference to interior chamber 135, the vaporization of vaporizable material 104 is enhanced by the location of receptacle 144 inside housing 124. Including receptacle 144 inside housing 124 reduces the possibility that a draft of air or other outside influence will cool or dislodge receptacle 144 from the process of vaporization. Additionally, increased heat uniformity is achieved, particularly in the embodiment where housing 124 includes bottom portion 156 (FIG. 3), lid 128 and flow director 240 (FIG. 4). Together, these structures surround receptacle 144, thus resulting in increased heat uniformity and the heating of vaporizable material 104 through convection and conduction.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A valve for use with a vaporizer having a structure for exhausting vapor, said valve comprising:
   a. a body having an opening for receiving the structure of the vaporizer;
   b. a clamping assembly located at least partially within said body so as to be in communication with said opening, wherein said clamping assembly is operable between a first position, in which said clamping assembly cooperates with the structure to releasably secure said body thereto when the structure is present in the opening, and a second position, in which said body may be moved freely on and off the structure;
   c. a mouthpiece in fluid communication with said opening so that vapor may be drawn through said opening via said mouthpiece; and
   d. a connector for securing a vapor-receiving container to said body proximate said opening.

2. A valve according to claim 1, wherein said clamping assembly is further operable from either of said first and second positions to a third position in which said clamping assembly blocks said opening.

3. A valve according to claim 2, wherein said clamping assembly includes a plug and a biasing member for urging said plug toward said third position.

4. A valve according to claim 2, wherein said clamping assembly is sized and configured to permit a user to move said clamping assembly with a single digit between said first, second, and third positions.

5. A valve according to claim 1, wherein said mouthpiece extends from said body.

6. A valve according to claim 1, wherein said clamping assembly is at least partially received within said body.

7. A valve according to claim 1, wherein at least a portion of said clamping assembly is operable to move along a linear axis.

8. A valve according to claim 7, the structure of the vaporizer having an elongate axis, wherein said linear axis extends perpendicularly with respect to the elongate axis when the structure is received in said opening of said body.

9. A valve according to claim 1, wherein said connector for securing said vapor-receiving container to said body is operable to secure said vapor-receiving container at least partially within said body.

10. A valve according to claim 1, wherein said body has a peripheral section that forms said mouthpiece.

11. A valve according to claim 1, wherein said body has an outer surface and said mouthpiece is coextensive with said outer surface of said body.

12. A valve according to claim 1, wherein at least a portion of the vaporizer is external to said body when the structure is present in said opening.

13. A valve for use with a vaporizer and a vapor container, the valve comprising:
   a body having:
      a first opening configured to receive a portion of the vaporizer; and
      a second opening configured to communicate with a portion of the vapor container;
   a clamping assembly located at least partially within said body, said clamping assembly operable to releasably engage said portion of the vaporizer in order to secure said body to said portion of the vaporizer; and
   a mouthpiece proximate said first opening.

14. A valve according to claim 13, wherein said clamping assembly is operable between a first position, in which said clamping assembly grips said portion of the vaporizer, and a second position, in which said clamping assembly does not grip said portion of said vaporizer.

15. A valve according to claim 14, wherein said clamping assembly is further operable from either of said first and second positions to a third position in which said clamping assembly blocks said second opening.

16. A valve according to claim 15, wherein said clamping assembly includes a plug and a biasing member for urging said plug toward said third position.

17. A valve according to claim 15, wherein said clamping assembly is sized and configured to permit a user to move said clamping assembly with a single digit between said first, second, and third positions.

18. A valve according to claim 13, further comprising a connector for securing said vapor container to said body proximate said second opening.

19. A valve according to claim 18, wherein said connector for securing said vapor container to said body is operable to secure said vapor container at least partially within said body.

20. A valve according to claim 13, wherein said mouthpiece extends away from said body.

21. A valve according to claim 13, wherein said clamping assembly is at least partially received within said body.

22. A valve according to claim 13, wherein at least a portion of said clamping assembly is operable to move along a linear axis.

23. A valve according to claim 13, the portion of the vaporizer having an elongate axis, wherein said linear axis extends perpendicularly with respect to the elongate axis of the portion of the vaporizer.

24. A valve according to claim 13, wherein said body has a peripheral section that forms said mouthpiece.

25. A valve according to claim 13, wherein said body has an outer surface and said mouthpiece is coextensive with said outer surface of said body.

26. A valve according to claim 13, wherein at least a portion of the vaporizer is external to said body when said clamping assembly secures said body to said portion of the vaporizer.

27. A valve for use with a vaporizer and a vapor container, the valve comprising:
   a body having:
      a first opening configured to receive a portion of the vaporizer; and
      a second opening configured to communicate with a portion of the vapor container;
   a clamping assembly disposed proximate said body, said clamping assembly operable to releasably secure said body to said portion of the vaporizer; and
   a mouthpiece proximate said first opening,
   wherein:
      said clamping assembly is operable between a first position, in which said clamping assembly grips said portion of the vaporizer, and a second position, in which said clamping assembly does not grip said portion of said vaporizer;
      said clamping assembly is further operable from either of said first and second positions to a third position in which said clamping assembly blocks said second opening; and
      said clamping assembly includes a plug and a biasing member for urging said plug toward said third position.

28. A valve for use with a vaporizer having a structure for exhausting vapor, said valve comprising:
   a. a body having an opening for receiving the structure of the vaporizer;
   b. a clamping assembly associated with said body so as to be in communication with said opening, wherein said clamping assembly is operable between a first position, in which said clamping assembly cooperates with the structure to releasably secure said body thereto when the structure is present in the opening, and a second position, in which said body may be moved freely on and off the structure, and said clamping assembly is further operable from either of said first and second positions to a third position in which said clamping assembly blocks said opening, further wherein clamping assembly includes a plug and a biasing member for urging said plug toward said third position;
   c. a mouthpiece in fluid communication with said opening so that vapor may be drawn through said opening via said mouthpiece; and
   d. a connector for securing a vapor-receiving container to said body proximate said opening.

29. A valve for use with a vaporizer having a structure for exhausting vapor, said valve comprising:
   a. a body having an opening for receiving the structure of the vaporizer;
   b. a clamping assembly associated with and at least partially received within said body so as to be in communication with said opening, wherein said clamping assembly is operable between a first position, in which said clamping assembly cooperates with the structure to releasably secure said body thereto when the structure is present in the opening, and a second position, in which said body may be moved freely on and off the structure;
   c. a mouthpiece in fluid communication with said opening so that vapor may be drawn through said opening via said mouthpiece; and
   d. a connector for securing a vapor-receiving container to said body proximate said opening.

30. A valve for use with a vaporizer having a structure for exhausting vapor, said valve comprising:
   a. a body having an opening for receiving the structure of the vaporizer;
   b. a clamping assembly associated with said body so as to be in communication with said opening, wherein said clamping assembly is operable between a first position, in which said clamping assembly cooperates with the structure to releasably secure said body thereto when the structure is present in the opening, and a second position, in which said body may be moved freely on and off the structure;

c. a mouthpiece in fluid communication with said opening so that vapor may be drawn through said opening via said mouthpiece; and d. a connector for securing a vapor-receiving container to said body proximate said opening, said connector operable to secure said vapor-receiving container at least partially within said body.

31. A valve for use with a vaporizer having a structure for exhausting vapor, said valve comprising:
 a. a body having an opening for receiving the structure of the vaporizer and an outer surface;
 b. a clamping assembly associated with said body so as to be in communication with said opening, wherein said clamping assembly is operable between a first position, in which said clamping assembly cooperates with the structure to releasably secure said body thereto when the structure is present in the opening, and a second position, in which said body may be moved freely on and off the structure;
 c. a mouthpiece coextensive with said outer surface of said body and in fluid communication with said opening so that vapor may be drawn through said opening via said mouthpiece; and
 d. a connector for securing a vapor-receiving container to said body proximate said opening.

32. A valve for use with a vaporizer and a vapor container, the valve comprising:
 a body having:
  a first opening configured to receive a portion of the vaporizer; and
  a second opening configured to communicate with a portion of the vapor container;
 a clamping assembly disposed proximate and at least partially received within said body, said clamping assembly operable to releasably engage said portion in order to secure said body to said portion of the vaporizer; and
 a mouthpiece proximate said first opening.

33. A valve for use with a vaporizer and a vapor container, the valve comprising:
 a body having:
  a first opening configured to receive a portion of the vaporizer; and
  a second opening configured to communicate with a portion of the vapor container;
 a connector for securing said vapor container to said body proximate said second opening, wherein said connector is operable to secure said vapor container at least partially within said body;
 a clamping assembly disposed proximate said body, said clamping assembly operable to releasably engage said portion in order to secure said body to said portion of the vaporizer; and
 a mouthpiece proximate said first opening.

34. A valve for use with a vaporizer and a vapor container, the valve comprising:
 a body having:
  a first opening configured to receive a portion of the vaporizer;
  a second opening configured to communicate with a portion of the vapor container; and
  an outer surface;
 a clamping assembly disposed proximate said body, said clamping assembly operable to releasably engage said portion in order to secure said body to said portion of the vaporizer; and
 a mouthpiece proximate said first opening and coextensive with said outer surface of said body.

\* \* \* \* \*